United States Patent
Hoffmann et al.

(10) Patent No.: US 9,974,632 B2
(45) Date of Patent: May 22, 2018

(54) METHOD FOR POSITIONING ARTIFICIAL POSTERIOR TEETH

(71) Applicant: Amann Girrbach AG, Koblach (AT)

(72) Inventors: Rita Hoffmann, Feldkirch (AT); Ineke Lindemann, Dornbirn (AT)

(73) Assignee: Amann Girrbach AG, Koblach (AT)

( * ) Notice: Subject to any disclaimer, the term of this patent is extended or adjusted under 35 U.S.C. 154(b) by 542 days.

(21) Appl. No.: 14/409,705

(22) PCT Filed: Jun. 11, 2013

(86) PCT No.: PCT/AT2013/000098
§ 371 (c)(1),
(2) Date: Dec. 19, 2014

(87) PCT Pub. No.: WO2013/188894
PCT Pub. Date: Dec. 27, 2013

(65) Prior Publication Data
US 2015/0327959 A1 Nov. 19, 2015

(30) Foreign Application Priority Data
Jun. 22, 2012 (DE) .......... 10 2012 012 507

(51) Int. Cl.
*A61C 9/00* (2006.01)
*A61C 13/00* (2006.01)
*A61C 13/36* (2006.01)

(52) U.S. Cl.
CPC .......... *A61C 9/002* (2013.01); *A61C 13/0004* (2013.01); *A61C 13/1016* (2013.01)

(58) Field of Classification Search
CPC .. A61C 13/0004; A61C 13/1016; A61C 9/002
(Continued)

(56) References Cited

U.S. PATENT DOCUMENTS 5,273,429 A 12/1993 Rekow et al.
7,153,135 B1 12/2006 Thomas
(Continued)

FOREIGN PATENT DOCUMENTS

DE 4008718 9/1991
DE 102005013459 10/2006
(Continued)

OTHER PUBLICATIONS

Korholz, K.-H.: "Totalprothetik in Funktion—Teil 1: Die Modellanalyse, Teil 2: Die Aufstellung des Unterkiefers, Teil 3: Die Aufstellung des Oberkiefers; (Full Dentures Prosthetic in Operation—Part 1: the model analysis, part 2: the arrangement of the lower jaw, part 3: the arrangement of the upper jaw)"; in QZ—Quintessenz Zahntechnik 26; 2000; 1, 9-21; 2, 101-114; 3. 201-213.
(Continued)

*Primary Examiner* — Eunhee Kim
(74) *Attorney, Agent, or Firm* — Volpe and Koenig, P.C.

(57) ABSTRACT

Method for positioning artificial posterior teeth (1, 2, 3, 4, 19, 20, 21, 22) on an entirely edentulous or at least partially edentulous jaw model (5, 6), wherein several artificial posterior teeth (1, 2, 3, 4, 19, 20, 21, 22) are combined to form at least one tooth block (7), wherein the artificial posterior teeth (1, 2, 3, 4, 19, 20, 21, 22) in this tooth block (7) are arranged in a fixed geometric relationship to one another, and geometric parameters of the tooth block (7) are established on the tooth block (7), and geometric parameters of the jaw model (5, 6) are established on the jaw model (5, 6), and, in order to position the tooth block (7) on the jaw model (5, 6), the geometric parameters of the tooth block (7) are assigned to the geometric parameters of the jaw model (5, 6).

9 Claims, 9 Drawing Sheets

(58) Field of Classification Search
USPC .......................................................... 703/1
See application file for complete search history.

(56) References Cited

U.S. PATENT DOCUMENTS

| | | |
|---|---|---|
| 2002/0110786 A1 | 8/2002 | Dillier |
| 2003/0003420 A1 | 1/2003 | Striezel |
| 2004/0175671 A1 | 9/2004 | Jones et al. |
| 2004/0185422 A1 | 9/2004 | Orth et al. |
| 2004/0219490 A1 | 11/2004 | Gartner et al. |
| 2006/0210945 A1 | 9/2006 | Savic et al. |
| 2006/0263749 A1* | 11/2006 | Koide ............... A61C 13/097 433/197 |
| 2007/0287131 A1 | 12/2007 | Ruppert et al. |
| 2009/0287332 A1 | 11/2009 | Adusumilli et al. |
| 2010/0086899 A1 | 4/2010 | Holzner et al. |
| 2010/0283168 A1* | 11/2010 | Vandor ............... A61C 13/34 264/17 |
| 2011/0318709 A1* | 12/2011 | Moriyama ......... A61C 13/0004 433/191 |
| 2012/0258430 A1 | 10/2012 | Ruppert et al. |

FOREIGN PATENT DOCUMENTS

| | | |
|---|---|---|
| DE | 102007002178 | 7/2008 |
| EP | 1269934 | 1/2003 |
| EP | 1444965 | 8/2004 |
| EP | 1459702 | 9/2004 |
| EP | 1621157 | 2/2006 |
| EP | 1864627 | 12/2007 |
| EP | 1621157 | 10/2010 |
| WO | 2009105661 | 8/2009 |
| WO | 2011066895 | 6/2011 |

OTHER PUBLICATIONS

Naumann, K.: "Experimental Comparison Study Regarding the Extent of Three-Dimensional Changes of the Position of Artificial Teeth in the Production of Full Dentures depending on the Different Processing Technologies"; dissertation; at: Friedrich-Schiller-University Jena; 2008, p. 1-105.

Sohnel, S.; "Qualitat rationeller Methoden zur Anfertigung von Zahnersatz in volliger Zahnlosigkeit (Quality of Rational Methods for Producing Dental Prostheses in Cases of Complete Toothlessness)"; in augural dissertation, at: Ernst-Moritz-Arndt-University Greifswald, 2001 (Disputation: Apr. 2, 2010); p. 21-30.

* cited by examiner

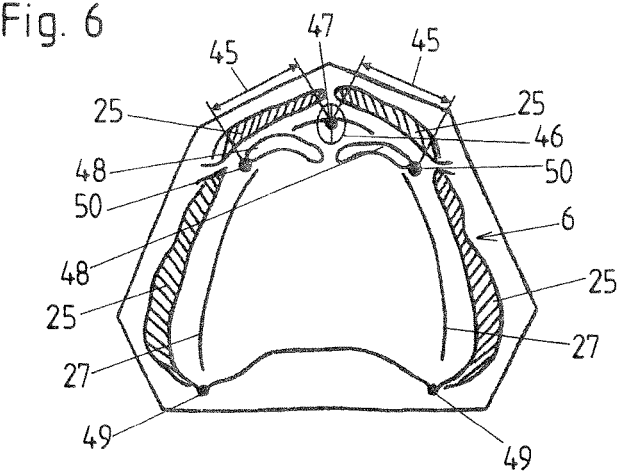
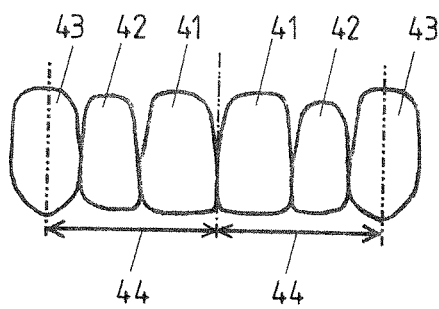
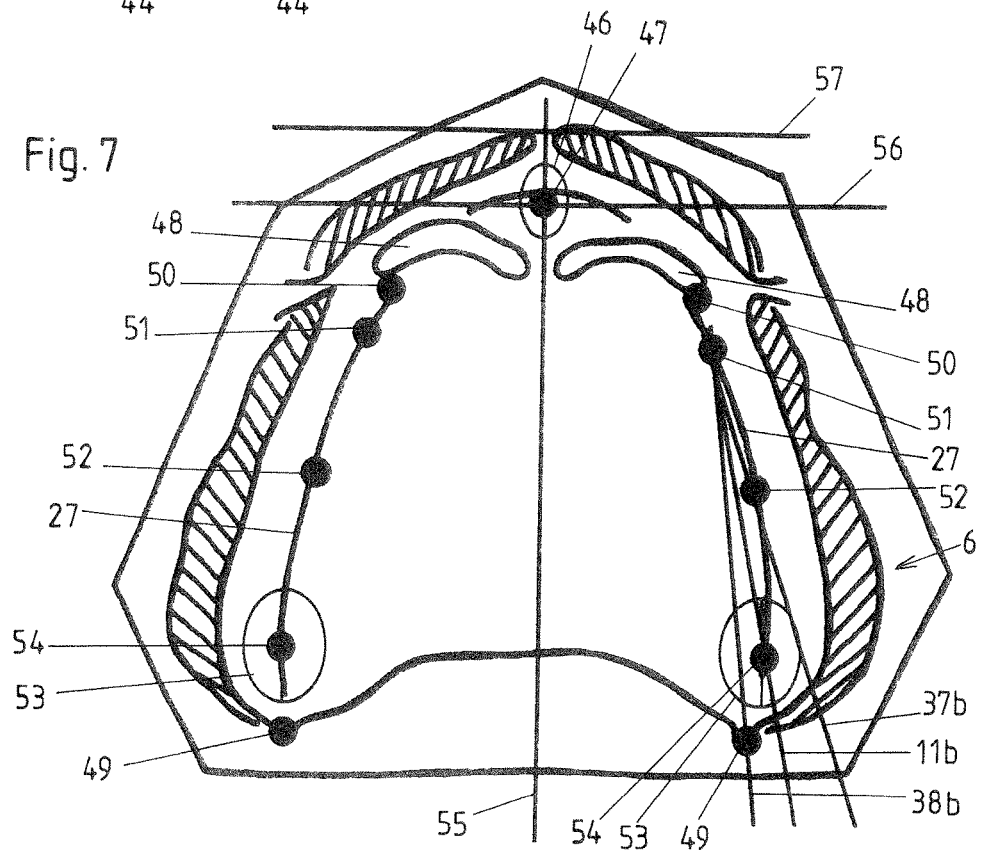

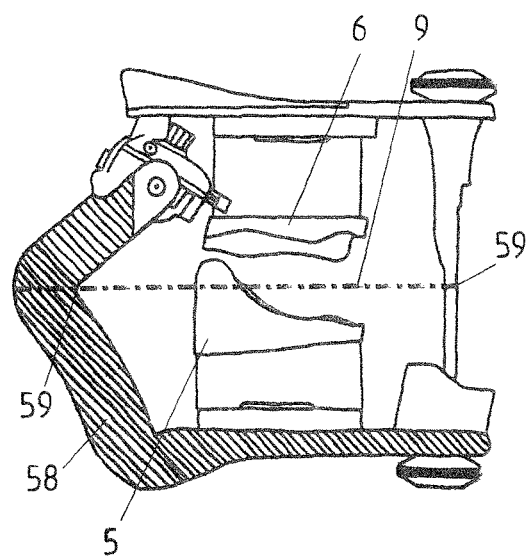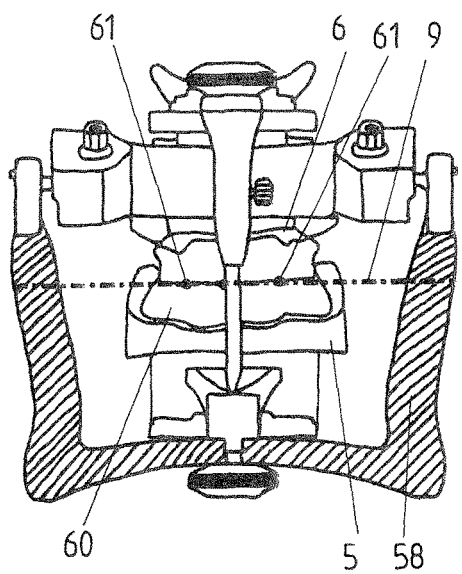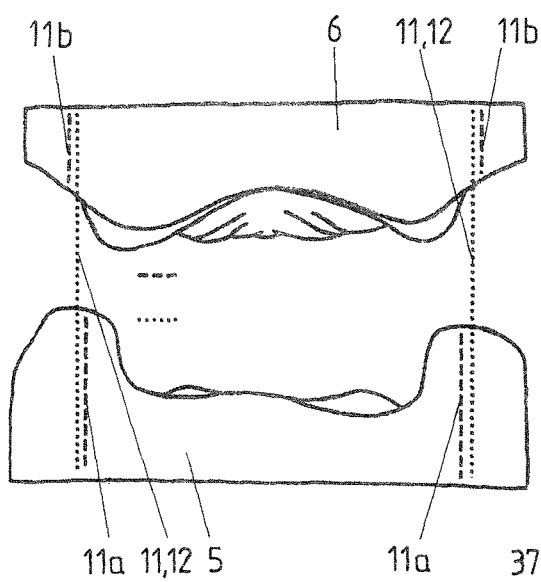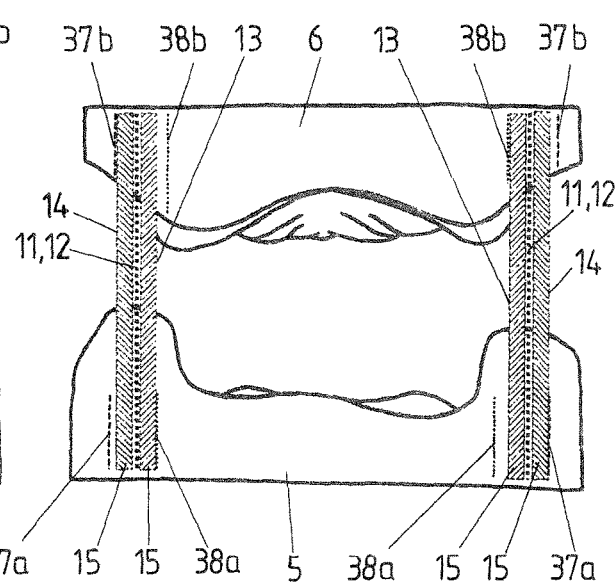

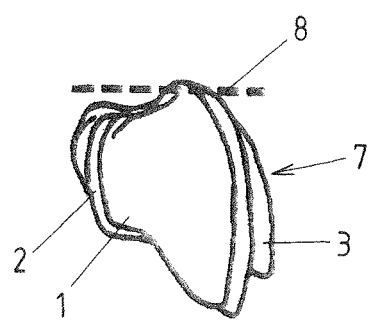
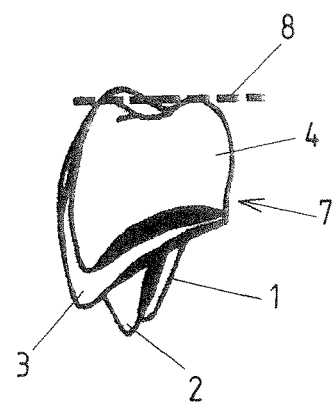
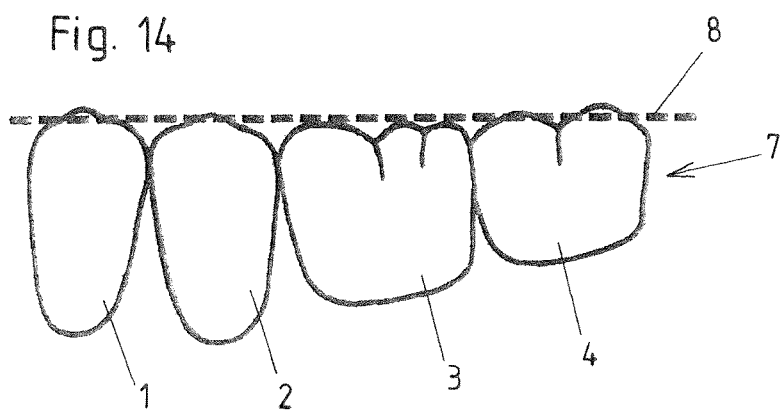
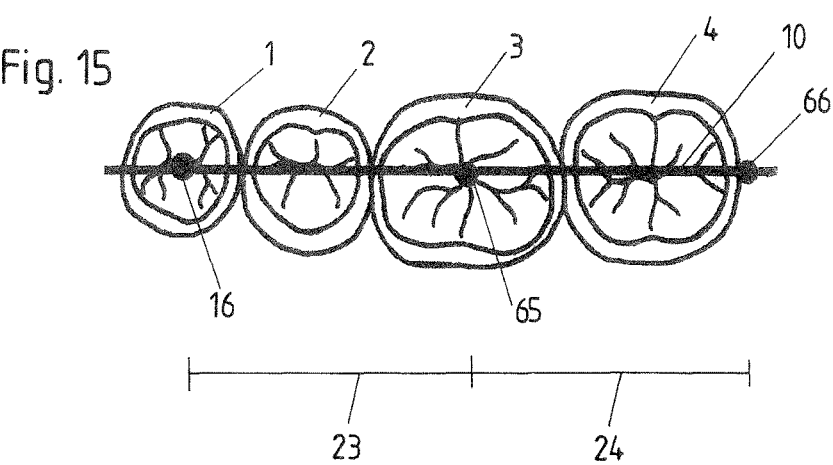

METHOD FOR POSITIONING ARTIFICIAL POSTERIOR TEETH

BACKGROUND

The present invention relates to a method for positioning artificial posterior teeth on an entirely edentulous or at last partially edentulous jaw model.

In the production of artificial tooth prostheses, the artificial teeth have to be positioned on an entirely edentulous or at least partially edentulous jaw model such that the prosthesis ultimately placed in the mouth of the patient is supported in a stable manner during mastication. To this end, it is important that the structure and shape of the prosthesis is adapted as well as possible to the natural static conditions in the mouth of the patient. While the artificial anterior teeth are also positioned especially with respect to visual and phonetic aspects, it is particularly important that the artificial posterior teeth are positioned accurately and correctly on the entirely edentulous or at least partially edentulous jaw model. If the artificial posterior teeth, either in terms of their position relative to the jaw or in terms of their position relative to one another, are incorrectly positioned with respect to occlusion, the prosthesis shifts within the oral cavity of the patient during mastication. In the prior art, the posterior teeth and also the anterior teeth are set up individually and are then adapted to one another as far as possible in their position. On the one hand, this is very difficult and, on the other hand, it does not always give an optimal result, particularly as regards the static requirements as mentioned.

SUMMARY

The object of the invention is therefore to make available a method of the type in question for positioning artificial posterior teeth, which method is particularly effective and saves the user time, and in which sufficient account is nonetheless taken of the static demands in the oral cavity of the patient.

According to the invention, this is achieved by a method.

Provision is thus made that several artificial posterior teeth are combined to form at least one tooth block, wherein the artificial posterior teeth in this tooth block are arranged in a fixed geometric relationship to one another, and geometric parameters of the tooth block are established on the tooth block, and geometric parameters of the jaw model are established on the jaw model, and, in order to position the tooth block on the jaw model, the geometric parameters of the tooth block are assigned to the geometric parameters of the jaw model.

Thus, an underlying concept of the invention is that the posterior teeth are no longer individually positioned one after another on the entirely edentulous or at least partially edentulous jaw model, and instead several artificial posterior teeth are arranged in a fixed geometric relationship to one another in a tooth block, and certain geometric parameters are assigned to this tooth block. This then makes it possible to position the whole tooth block on the jaw model, by assigning the geometric parameters of the tooth block to the geometric parameters of the jaw model. In this way, all the posterior teeth brought together in this tooth block are positioned simultaneously. This can be done very quickly and effectively by the user. However, it also avoids errors in the tooth positioning. A tooth block comprises several posterior teeth, i.e. at least two, preferably at least three or four posterior teeth per jaw quadrant. The tooth block can exclusively comprise posterior teeth for the lower jaw or exclusively posterior teeth for the upper jaw. However, in particularly preferred embodiments, the tooth block comprises both posterior teeth of the lower jaw and also, assigned thereto, posterior teeth of the upper jaw. These assigned posterior teeth are what are called the antagonists. Particularly preferably, the tooth block comprises three or four artificial posterior teeth for the lower jaw and/or the upper jaw. If it comprises teeth both for the upper jaw and also for the lower jaw, these are in each case the posterior teeth of the lower jaw and their antagonists in the upper jaw. Such tooth blocks then expediently comprise six or eight artificial posterior teeth. If the tooth block comprises both artificial posterior teeth of the lower jaw and also those of the upper jaw, then the posterior teeth are expediently arranged bearing on each other in the bite position or occlusion position in the tooth block.

The posterior teeth can also be referred to as molars. In dentistry, these posterior teeth are designated as the fourth tooth, fifth tooth, sixth tooth and seventh tooth. The wisdom teeth or eighth teeth are generally not set up in the manufacture of prostheses. The anterior teeth mentioned further below are to be distinguished from the posterior teeth. In dentistry, and also in the description below, they are designated as the first, second and third teeth. The first teeth are the central incisors, the second teeth are the lateral incisors, and the third teeth are the canines. The first posterior tooth is the fourth tooth, which adjoins the third tooth.

The entirely or at least partially edentulous jaw model can be generated or produced digitally by scanning within the mouth, by scanning of an impression, by scanning the jaw model itself, or in another known way. It can be in the form of a digital data model or an actual physical model. It at least partially reproduces the shape of the prosthesis base or can itself already be the physically present prosthesis base. The prosthesis base is the part of the subsequent prosthesis which, during the intended use of the prosthesis, bears directly on the alveolar ridge and on the soft-tissue parts of the patient or prosthesis wearer that delimit the oral cavity.

Methods according to the invention are expediently carried out digitally or at least partially digitally on a computer. This results in digital jaw models, posterior teeth and tooth blocks. As has been stated, the jaw models are obtained by suitable scanning or impression-taking in the mouth of the patient, or on models of the mouth of the patient. For the individual posterior teeth, there are already artificial posterior teeth that can be purchased on the market both in digital form and also as actual physical teeth.

Particularly preferably, the method according to the invention is used in CAD-CAM technology. Provision is preferably made that the several artificial posterior teeth are removed as a digital data set from a digital databank. It is also preferable if the artificial posterior teeth are combined digitally as a data set to form one tooth block. The determination of the geometric parameters of the tooth block on the tooth block and/or the determination of the geometric parameters of the jaw model on the jaw model can also be carried out digitally, preferably interactively with the user. Moreover, the assignment of the geometric parameters of the tooth block to the geometric parameters of the jaw model can also take place digitally, preferably fully automatically. The word digitally here refers to a computer-aided procedure or to the performance of the method step on a computer.

On the basis of a jaw model that is digitally generated according to the invention, and on the basis of posterior teeth positioned digitally thereon, it is accordingly possible to produce an actual physical prosthesis. It is possible in principle that the prosthesis comprises both the prosthesis base and also the posterior teeth, and if appropriate also the anterior teeth, in one piece. It is thus possible, for example, for the entire prosthesis to be produced by cutting methods known per se or also by additive methods known per se. Particularly preferably, however, provision is made that, on the basis of the digital model of the jaw, a corresponding prosthesis base is created by cutting methods or additive methods known per se, or by other suitable methods, and the accordingly prepared commercially available posterior teeth are then accordingly positioned on or inserted into the prosthesis base. For this purpose, it may be necessary for the posterior teeth to be shortened beforehand. The methods for producing actual physical prostheses of this kind that are then fitted in the mouth of the patient are known per se in the prior art.

With the method according to the invention, the user can be provided with a library or databank of prefabricated tooth blocks along with information concerning their corresponding geometric parameters. On the market, various manufacturers offer different tooth shapes and sizes in the form of artificial teeth which, according to the invention, can then be combined to form a tooth block and can then be used as such. From this library, the user can then choose a suitable tooth block on the basis of certain geometric parameters. However, the choice of the suitable tooth blocks can also be automated on the basis of said geometric parameters of the tooth block and of the jaw model. For example, provision can be made that the choice of the tooth block with the posterior teeth is made according to the geometric parameters of the jaw model of the lower jaw and the choice of the matching anterior teeth depends on the geometric parameters of the upper jaw model. The matching antagonists depend in each case on the chosen posterior teeth and anterior teeth. The positioning is then fully automated or partially automated, via the assignment of the geometric parameters of the tooth block to the geometric parameters of the individual jaw model. If appropriate, an individual adjustment is then also possible within certain predefined tolerance ranges. However, it is in particular possible for the artificial posterior teeth of the upper jaw and lower jaw, which have been combined in one tooth block, to be simultaneously positioned on the articulated upper jaw model and lower jaw model of the patient, by assigning the geometric parameters of this tooth block to the geometric parameters of a jaw model of the patient.

For the sake of completeness, it will be noted that the method according to the invention can also be carried out in a fully analog manner, i.e. without the aid of a computer. An actual physical prosthesis base, for example, can then be used as jaw model. The artificial posterior teeth can be joined together on the tooth block by easily detachable adhesive or contact agents. The determination of the geometric parameters of the jaw model and of the tooth block, which parameters are required for the assignment according to the invention, and the assignment according to the invention by means of these geometric parameters, also take place unchanged in the purely analog application.

The geometric parameters of the jaw model reproduce natural conditions within the oral cavity of the patient, insofar as these are of importance for the positioning of the artificial posterior teeth or of the tooth block. The geometric parameters or characteristics of the jaw model can be determined as known per se by so-called model analysis. In principle, various geometric parameters of the tooth block and of the jaw model can be used in the method according to the invention. The number of the required parameters can also vary.

In preferred embodiments of the invention, the geometric parameters of the tooth block are made congruent with the geometric parameters of the jaw model when positioning the tooth block on the jaw model.

In particularly preferred variants of the invention, the jaw model is a jaw model of the lower jaw and the tooth block has artificial posterior teeth at least for the lower jaw. It is possible in principle, and also preferable, if the tooth block comprises artificial posterior teeth for the lower jaw and, assigned to these, artificial posterior teeth for the upper jaw. The positioning of such a tooth block on the jaw model of the lower jaw also automatically has the result that the artificial posterior teeth contained in the tooth block for the upper jaw are correctly positioned on the articulated jaw model of the upper jaw. The tooth block expediently comprises at least three or four artificial posterior teeth for the lower jaw. If it also contains artificial posterior teeth for the upper jaw, then the number thereof expediently corresponds to the number of the artificial posterior teeth for the lower jaw. These are indeed the corresponding antagonists.

In a preferred embodiment of the invention, provision is made that a geometric parameter of the tooth block is a tooth block occlusion plane common to the artificial posterior teeth of the tooth block, and a geometric parameter of the jaw model is a jaw model occlusion plane assigned to the jaw model, and, when this tooth block is positioned on the jaw model, the tooth block occlusion plane is placed in the jaw model occlusion plane. Provision can further be made that a geometric parameter of the tooth block is a preferably straight main fissure line common to the artificial posterior teeth of this tooth block, and a geometric parameter of the jaw model is a preferably straight base static line assigned to the jaw model, and, when the tooth block is positioned on the jaw model, the main fissure line and the base static line are arranged in a common base static plane. The base static plane is preferably arranged orthogonally on the jaw model occlusion plane. If the tooth block comprises artificial posterior teeth for the lower jaw and also for the upper jaw, then the base static line is expediently a common base static line of the jaw model of the lower jaw and of the upper jaw. To provide the person using the method with a certain amount of individual play, provision can be made that the base static plane is assigned a tolerance range, which is limited preferably by correction planes likewise arranged orthogonally on the jaw model occlusion plane, and in which deviations of the main fissure line from the base static plane are permitted.

Preferred methods according to the invention can also be provided in which a geometric parameter of the tooth block is a tooth 4 position assigned to an artificial 4th tooth of the tooth block, and a geometric parameter of the jaw model is a jaw model 4th position assigned to the jaw model, and, when the tooth block is positioned on the jaw model, the tooth 4 position and the jaw model 4th position are arranged on a common 4th straight line, provision preferably being made that the 4th straight line is arranged perpendicularly on the jaw model occlusion plane.

BRIEF DESCRIPTION OF THE DRAWINGS

A preferred illustrative embodiment of the method according to the invention is explained below in the description of the figures. An explanation is then given of how, in addition, anterior teeth can also be positioned. In the figures:

FIG. 5 shows artificial anterior teeth;

FIGS. 6 and 7 show plan views of a jaw model of the upper jaw;

FIGS. 8 and 9 show views, from the side and from the front, of an articulator with articulated jaw models of the lower jaw and upper jaw;

FIGS. 10 and 11 show rear views of the articulated jaw models of the lower jaw and upper jaw;

FIGS. 12 to 15 show different views of the artificial posterior teeth for the lower jaw of a tooth block;

DETAILED DESCRIPTION OF THE PREFERRED EMBODIMENTS

Figure 1:
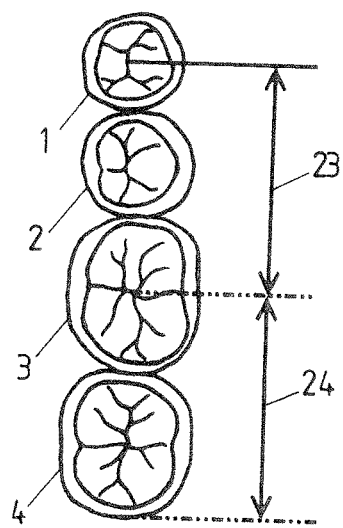
FIG. 1 shows a tooth block with four artificial posterior teeth.

A tooth block 7 with four artificial posterior teeth 1 to 4 for the lower jaw is shown schematically in FIG. 1. The artificial posterior tooth 1 is the so-called fourth tooth, i.e. the first posterior tooth or molar, which follows the canine or third tooth of the anterior teeth. It is followed in turn by the fifth tooth as artificial posterior tooth 2, the sixth tooth as artificial posterior tooth 3, and the seventh tooth as artificial posterior tooth 4. In preferred embodiments of the invention, the tooth block 7 comprises the four artificial posterior teeth 1 to 4 of the lower jaw. However, if not enough space is available, the tooth block 7 can also comprise only the first three teeth, i.e. the fourth, fifth and sixth teeth, and therefore the artificial posterior teeth 1 to 3. Moreover, if there is lack of space, it is also possible that the tooth block 7 contains only the artificial posterior teeth 1, 3 and 4. In this preferred illustrative embodiment of the invention shown here, the criteria for choosing how many and which posterior teeth should ultimately be positioned in the dentition are, on the one hand, the distance 23 from the center of the fourth tooth 1, or its tooth 4 position 16, to the center of the sixth tooth 3, or its tooth 6 position 65, and the distance 24 between the center of the sixth tooth 3, or its tooth 6 position 65, and the rear end or distal surface of the seventh tooth 4 or the tooth endpoint 66. In the illustrative embodiment shown, these distances 23 and 24 of the jaw model 5 of the lower jaw, and the distances 29 and 30 explained further below, are used to choose a suitable tooth block 7 and also to determine whether the latter comprises three or four artificial posterior teeth 1 to 4 of the lower jaw. However, this is explained again in greater detail further below.

Figure 2:
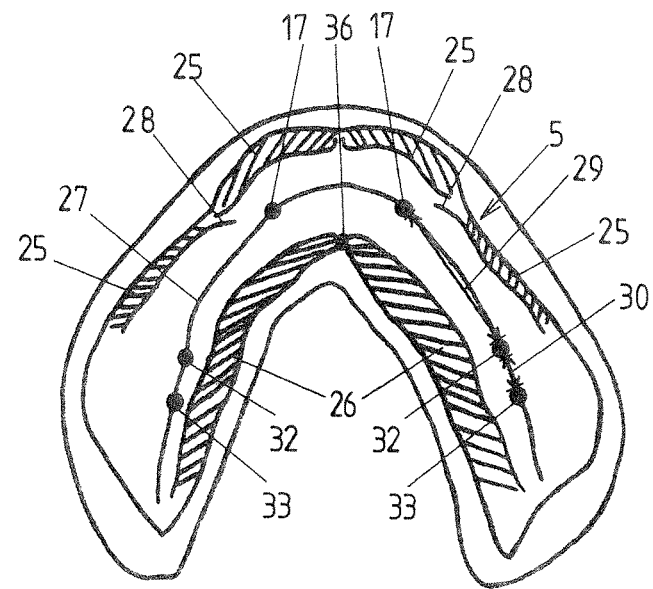
FIGS. 2 and 3 show plan views of a jaw model of the lower jaw.
Figure 3:
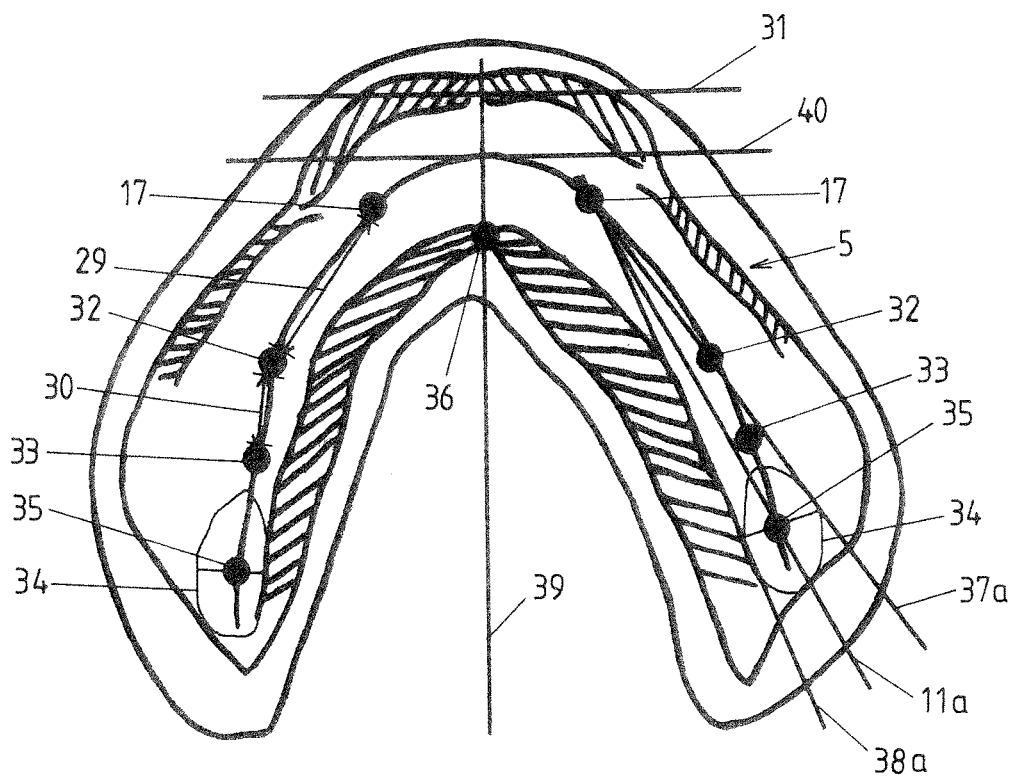

FIGS. 2 and 3 show a plan view of an example of a jaw model 5 of the lower jaw. FIG. 2 shows various properties or parameters to be determined on this jaw model 5, which are the starting point for the model analysis explained in more detail with reference to FIG. 3. The geometric parameters of the jaw model 5 that are needed in this illustrative embodiment, for the assignment according to the invention, are determined using the model analysis. The parameters shown in FIG. 2 are known anatomical features in dentistry which can be visually discerned on the jaw model and which form the basis of the subsequent model analysis. The jaw model 5 at least partially reproduces the surface contour of the edentulous lower jaw of the patient or of the prosthesis base to be produced. According to the invention, the posterior teeth 1 to 4 shown by way of example in FIG. 1 are now to be positioned on this jaw model 5 of the lower jaw. The corresponding posterior teeth 1 to 4, or 1 to 3, are positioned on both sides. This is done in a corresponding way on both sides, without this having to be explicitly set out twice hereinbelow.

Figure 4:
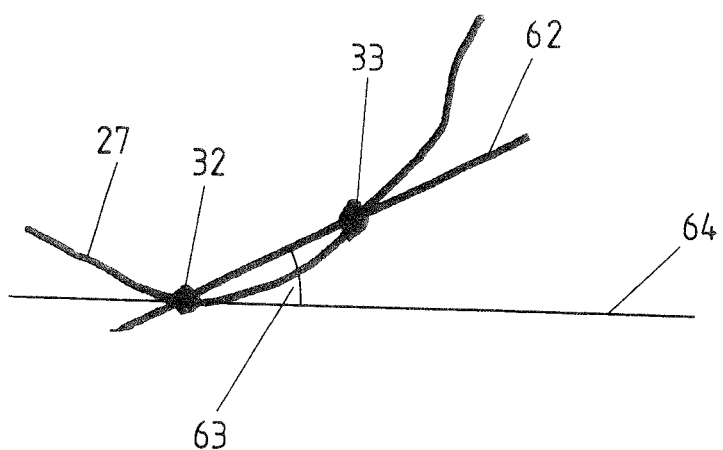
FIG. 4 shows a side view of the alveolar ridge profile of the lower jaw according to FIGS. 2 and 3.

The inner mucolabial fold 26 and the outer mucolabial fold 25 of the jaw model 5 will first be seen in FIG. 2. Between them, the alveolar ridge profile 27 can be clearly seen. The buccal frenum is designated by 28. The jaw model 4th position 17, in this illustrative embodiment of the jaw model 5 of the lower jaw, is determined by the continuation of the buccal frenum 28 as far as the alveolar ridge profile 27, at the intersection resulting there. Reference sign 32 designates the lower jaw 6th position. This is determined, in the side view shown in FIG. 4, as the deepest point on the alveolar ridge profile 27 and likewise lies on the alveolar ridge profile 27. The mandibular jaw endpoint 33 is determined on the basis of the side view of the alveolar ridge profile 27 shown in FIG. 4, by drawing the straight line 62, at an angle 63 of 22.5° to a parallel 64, to the jaw model occlusion plane 9, described further below, through the lower jaw 6th position 32. The mandibular endpoint 33 is then situated at the second or upper intersection of the straight line 62 with the alveolar ridge profile 27. In the variant of the invention shown, the distance 29 between the jaw model 4th position 17 and the lower jaw 6th position 32 and the distance 30 between the lower jaw 6th position 32 and the mandibular endpoint 33 are then used to choose a suitable tooth block 7 by comparing them with the distances 23 and 24 shown in FIG. 1, which were determined on the tooth block 7 with the artificial posterior teeth. If the distance 23 agrees with the distance 29 and the distance 24 agrees with the distance 30 within predefinable tolerance ranges, the tooth block 7 with these distances 23 and 24 is then suitable for being positioned on the jaw model 5 at the distances 29 and 30. If the distance 30 is below a certain minimum value, a decision can also be made that a tooth block 7 with only three artificial posterior teeth 1 to 3 for the lower jaw and, if appropriate, the corresponding antagonists for the upper jaw is positioned on this jaw model at the corresponding side. In this case, the respective seventh tooth 4 or 22 is then omitted in the tooth block 7. It is preferable for no further tooth to be positioned behind the mandibular endpoint 33.

On the lower jaw model 5, the mandibular lingual frenum 36 is then marked at the contact point of the two inner mucolabial folds 26, and the respective trigone 34 is marked at the respective rear end of the alveolar ridge profile 27. The points 35 are in each case the center points of the trigones 34. The base static line 11a of the jaw model 5 of the lower jaw is established by a straight connection between the jaw model 4th position 17 and the center point 35 of the trigone 34. The mandibular outer correction line 37a results from connecting the outer boundary of the trigone 34 to the jaw model 4th position 17. The mandibular inner correction line 38a results from connecting the inner boundary of the trigone 34 to the jaw model 4th position 17. These are in each case straight lines. The mandibular center line 39 extends through the center between the two center points 35 of the trigones 34 and the mandibular lingual frenum 36. The mandibular ridge center line 40 lies orthogonally on the mandibular center line 39 and cuts the latter at the intersection with the alveolar ridge profile 27. The frontal mandibular labial surface limit line 31 intersects the mandibular center line 39 again orthogonally, specifically at the lowest point of the outer mucolabial fold 25.

With this, all the steps of the model analysis that are needed for the further progress of the described embodiment of the method according to the invention are concluded on the jaw model 5 of the lower jaw. As has been stated, the distances 29 and 30 are needed for the selection of a suitable tooth block 7. The base static line 11a and the mandibular outer correction line 37a and mandibular inner correction line 38a serve for the subsequent positioning of the tooth block 7 of the artificial posterior teeth, just like the jaw model 4th position 17. The frontal mandibular ridge center line 40 and the frontal mandibular labial surface limit line 31 serve for the positioning of the anterior teeth. The latter does not directly concern the positioning of the posterior teeth but, for the sake of completeness, is explained by way of example at the end of the description. It should also be noted that, although part of the analysis is shown in FIG. 3 only for one side, the corresponding analysis and determination of the parameters takes place correspondingly on both sides, as long as corresponding tooth blocks 7 with corresponding artificial posterior teeth are also intended to be positioned on both sides.

FIG. 5 shows artificial anterior teeth. These are the artificial first front teeth 41, second front teeth 42 and third front teeth 43 for the upper jaw. The distances 44 run between the mesial contact point of the artificial first anterior teeth 41 and the respective tooth centers of the third front teeth or canines 43. FIGS. 6 and 7 in turn show corresponding plan views of a jaw model 6. However, this jaw model 6 is that of the upper jaw. The outer mucolabial folds 25 and the alveolar ridge profile 27 can be seen, and also the first greater palatine folds 48. Reference sign 47 designates the center point of the incisive papilla 46. The upper jaw 3rd position 50 is located at the respective outer ends of the first greater palatine folds 48. The respective distance between the upper jaw 3rd position 50 and the center point of the incisive papilla 46 is designated by 45. The points 49 of the pterygomandibular fold 49 are each located at the rear end of the upper jaw model 6. During the continuation of the model analysis on the upper jaw model 6, the respective upper jaw 4th position 51 can then be plotted on the respective alveolar ridge profile 27. It is spaced apart from the upper jaw 3rd position 50 by half the width of a 4th maxillary tooth. The upper jaw 6th position 52 is generated from the lower jaw 6th position 32 by orthogonal projection of articulated upper jaw model 6 and lower jaw model 5 orthogonally with respect to the jaw model occlusion plane 9 and corresponding intersection with the alveolar ridge profile 27 of the upper jaw model 6. The tuber 53 can be plotted on the upper jaw model as is known per se. Reference sign 54 designates the center point of this tuber 53. The base static line 11b of the jaw model 6 of the upper jaw is plotted by straight connection of this center point 54 of the tuber 53 to the upper jaw 4th position 51. The maxillary outer correction line 37b is obtained by connecting the upper jaw 4th position 51 to the upper jaw 6th position 52. The maxillary inner correction line 38b is obtained by connecting the upper jaw 4th position 51 to the pterygomandibular fold 49. This is done in the same way on both sides if corresponding data are needed for both sides of the jaw model 6. For the positioning of anterior teeth, the maxillary center line 55 can then also be generated by connecting the center between the two center points 54 of the tuber 53 to the center point 47 of the incisive papilla 46. The frontal maxillary ridge center line 56 is then determined by plotting a line, extending orthogonally with respect to the maxillary center line 55, at the center point 47 of the incisive papilla 46. The maxillary labial surface limit line 57 extends parallel to the frontal maxillary ridge center line 56, at a distance of 8 mm in the labial direction. Here too, all the lines mentioned are formed as straight lines. With this, the model analysis on the upper jaw model 6 is also concluded. The dimensions that are important for the choice of the maxillary anterior teeth are the distance 44 determined on the artificial anterior teeth and also the distance 45 on the upper jaw model 6 from the model analysis. The suitable tooth width for the set of maxillary anterior teeth is chosen on the basis of these distances. Moreover, the head shape, the physique or the width of the nose of the patient can be used as reference value; the correct tooth length for the set of maxillary anterior teeth depends on the available occlusal space and can be determined from the distance between the jaw model occlusion plane 40 and the frontal maxillary ridge center line 56. Each set of maxillary anterior teeth is assigned a matching set of mandibular anterior teeth which can be automatically loaded digitally.

FIG. 8 shows by way of example the jaw model 5 of the lower jaw and the jaw model 6 of the upper jaw articulated in an articulator 58. The articulation procedure is known per se and need not be further described. The jaw model occlusion plane 9 can then be established, preferably digitally, in the articulator 58. This can take place, as shown in FIG. 8, on articulated models using suitable markings 59 on the articulator 58. An alternative procedure, likewise known in the prior art, is to determine the jaw model occlusion plane 9, as shown in FIG. 9, by means of suitable markings 61, e.g. three points on a bite plate 60 between jaw model 5 of the lower jaw and jaw model 6 of the upper jaw. Other ways of determining the jaw model occlusion plane 9 that are known per se in the prior art can also be used. The determination of the jaw model occlusion plane 9 and also the articulation of the jaw models 5 and 6 are known both in a digital and also an analog procedure.

FIGS. 10 and 11 now show the jaw model 5 of the lower jaw and the jaw model 6 of the upper jaw in an articulated position with respect to each other, in each case from the dorsal direction. FIG. 10 shows the base static lines 11a of the jaw model 5 of the lower jaw and 11b of the jaw model 6 of the upper jaw, said lines having been determined, as described above, with the model analysis. As is also shown here, these lines do not necessarily have to be congruent with each other. For the further course of the method, the common base static line 11 shown here is then expediently determined from the jaw model 5 of the lower jaw and the jaw model 6 of the upper jaw. As is the case here for example, this line can be the center line between the two base static lines 11a and 11b, i.e. a kind of averaged base static line. This also gives the course of the base static plane 12, which is normal or orthogonal to the jaw model occlusion plane 9 and extends through the base static line 11. In preferred embodiments, tolerance ranges 15 can be assigned to the base static plane 12, e.g. by correction planes 13 and 14 arranged orthogonally on the jaw model occlusion plane 9, within which tolerance ranges 15 deviations from the base static plane 12 are allowed in the subsequent allocation of the main fissure line 10. These tolerance ranges 15 are indicated by dashed lines in FIG. 11. They are delimited by the correction planes 13 of the inner correction lines and correction planes 14 of the outer correction lines. The correction planes 13 and 14 once again lie normally or orthogonally with respect to the jaw model occlusion plane 9. To determine the correction planes 13 and 14, the mandibular outer correction lines 37a and maxillary outer correction lines 37b and the mandibular inner correction lines 38a and maxillary inner correction lines 38b are used that lie closest to the base static line 11 or base static plane 12. This is shown in FIG. 11. In preferred embodiments, provision is made that all contact points between the antagonists of the respective tooth block 7 have to lie within this tolerance range 15. If they do not do this, then the deviation of the main fissure line 10, described below, from the common base static plane 12 is no longer admissible.

In the depicted illustrative embodiment of the method according to the invention, all the necessary geometric parameters of the jaw model are thereby determined.

We explain below how, in this illustrative embodiment, the geometric parameters of the tooth block 7 of the invention that are needed for the assignment according to the invention are established. If they were determined in advance, the geometric parameters of the tooth blocks 7 can be stored for the user in a databank, from which the user then only needs to retrieve them. This is explained now with reference to FIGS. 12 to 15. First of all, each artificial posterior tooth 1 to 4 of the lower jaw is assigned to the common tooth block occlusion plane 8, or, if only three artificial posterior teeth of the lower jaw are to be assigned to the tooth block 7, only teeth 1 to 3. For this purpose, corresponding information is available for each tooth. For example, some manufacturers of artificial teeth indicate the distances of certain fixed points on the mastication surface of the artificial teeth from the occlusion plane. Thereafter, it is possible to establish the common main fissure line 10, shown in the plan view in FIG. 15, on the four posterior teeth 1 to 4. In the fifth, sixth and seventh teeth 2, 3 and 4, the common main fissure line 10 runs on the respective main fissure lines of these teeth. If appropriate, some averaging has to be carried out. In the fourth tooth 1, it runs between the buccal cusp and the main fissure line of this artificial fourth tooth 1. The distances are then determined between the artificial posterior teeth 1 to 4 thus arranged with respect to the common tooth block occlusion plane 8 and arranged in series along the common main fissure line 10. It is thus possible, for example, to provide a variable distance of 0 to 1 mm between each of the adjacent teeth 1 to 4.

The tooth 4 position 16 shown in FIG. 15 is then established. It lies on the highest point of the buccal cusp of the fourth posterior tooth 1. The tooth 6 position 65 is then established. It lies at the mastication center of the artificial sixth posterior tooth 3 and on the main fissure line 10; in the case of a four-tooth tooth block, the tooth endpoint 66 is at the distal end of the seventh posterior tooth 4 and lying on the main fissure line 10, and, in the case of a three-tooth tooth block, at the distal end of the sixth posterior tooth 3 and on the main fissure line 10. The distance between the tooth 4 position 16 and the tooth 6 position 65 yields the distance 23 already mentioned in the introduction, and the distance between the tooth 6 position 65 and the tooth endpoint 66 yields the distance 24 already mentioned in the introduction. As has already been explained, the distances 23 and 24 form the selection criteria as to which tooth block 7 is to be positioned in the respective situation in the oral cavity of the patient. Within predetermined tolerances, the distance 23 of the respective tooth block must correspond to the distance 29 of the lower jaw model 5 determined in the model analysis as described above. If four posterior teeth 1 to 4 of the lower jaw are intended to be present in the tooth block 7, the distance 24 must correspond to the distance 30 of the lower jaw model 5. In preferred variants of the invention, a collection of different tooth blocks 7, with different posterior teeth 1 to 4 or 1 to 3 of the lower jaw and, if appropriate, with corresponding antagonists of the upper jaw 19 to 22 or 19 to 21, is made available to the user in a databank, from which, by comparing said distances, he can then select the tooth block 7 suitable for the particular case in question.

Figure 16:
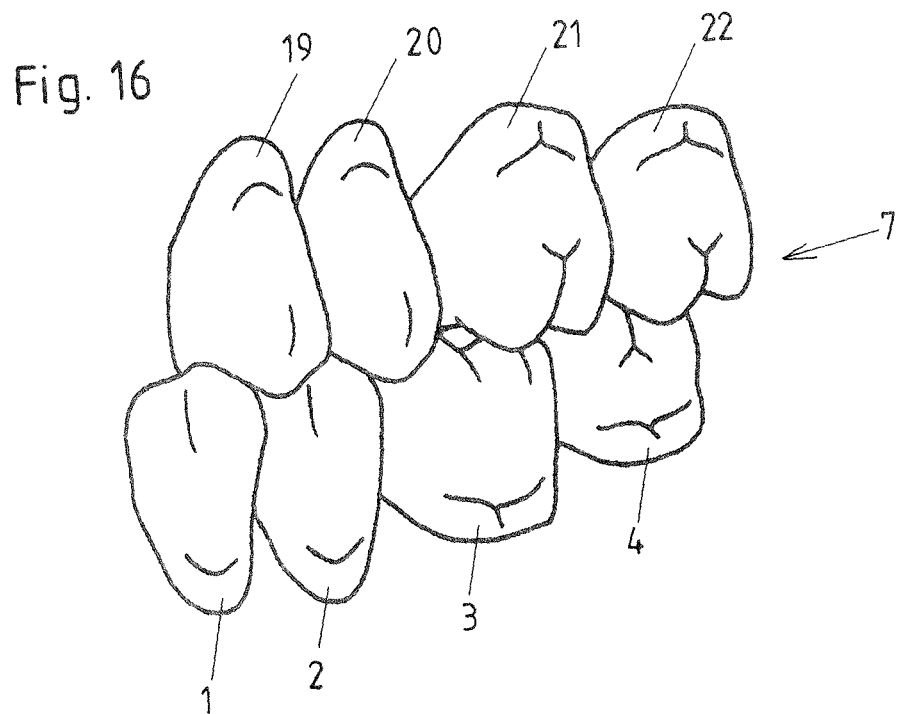
FIG. 16 shows a whole tooth block with the antagonists of the upper jaw.
Figure 17:
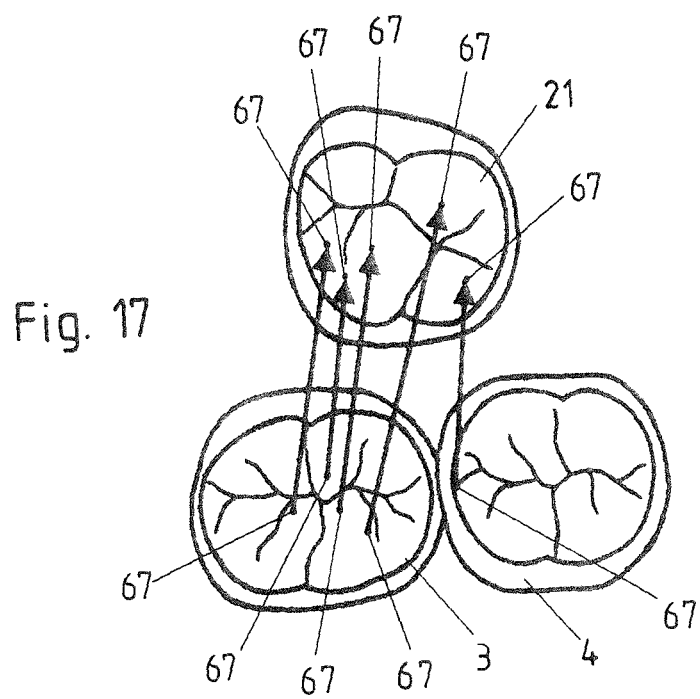
FIG. 17 shows a symbolized drawing of the mutual assignment of the antagonists.

FIG. 16 now shows by way of example a tooth block 7 with four artificial posterior teeth 1 to 4 of the lower jaw and with four artificial posterior teeth 19 to 22 of the upper jaw. The posterior teeth 1 to 4 and 19 to 22 are arranged in a fixed geometric relationship to one another in the tooth block 7. This is the bite position or occlusion position, in which the respective antagonists bear on each other via their occlusal contact points 67. The assignment of the respective antagonists, i.e. posterior teeth of the lower jaw to the associated posterior teeth of the upper jaw, can take place, as is known per se, using the known occlusal contact points 67 or those indicated by the manufacturer of the artificial posterior teeth, as is shown by way of example in FIG. 17. Through the assignment of the posterior teeth 19 to 22 via their occlusal contact points 67 to the posterior teeth 1 to 4, the position of the posterior teeth 19 to 22 is also clearly assigned to the geometric parameters of the tooth block 7 that are determined on the basis of the artificial posterior teeth 1 to 4 of the lower jaw. The determination of the geometric parameters of the different tooth blocks 7 likewise expediently takes place in advance and is preferably made available in a databank for the corresponding tooth blocks 7, such that, for the tooth block 7 determined on the basis of the abovementioned distances, the geometric parameters thereof that are required for the assignment to the jaw model are also automatically made available. In the illustrative embodiment explicitly shown here, the required geometric parameters of the tooth block 7 are the tooth block occlusion plane 8, the common main fissure line 10 and the tooth 4 position 16. The geometric parameters of the jaw model 5 that are required in this illustrative embodiment for the assignment according to the invention are the jaw model occlusion plane 9, the common base static line 11 and the jaw model 4th position 17. The tooth endpoint 66 and the mandibular endpoint 33 do not have to lie exactly congruently on each other. The tooth endpoint 66 at the distal end of the sixth posterior tooth 3 or seventh posterior tooth 4 should in each case lie in front of the mandibular endpoint 33.

Figure 18:
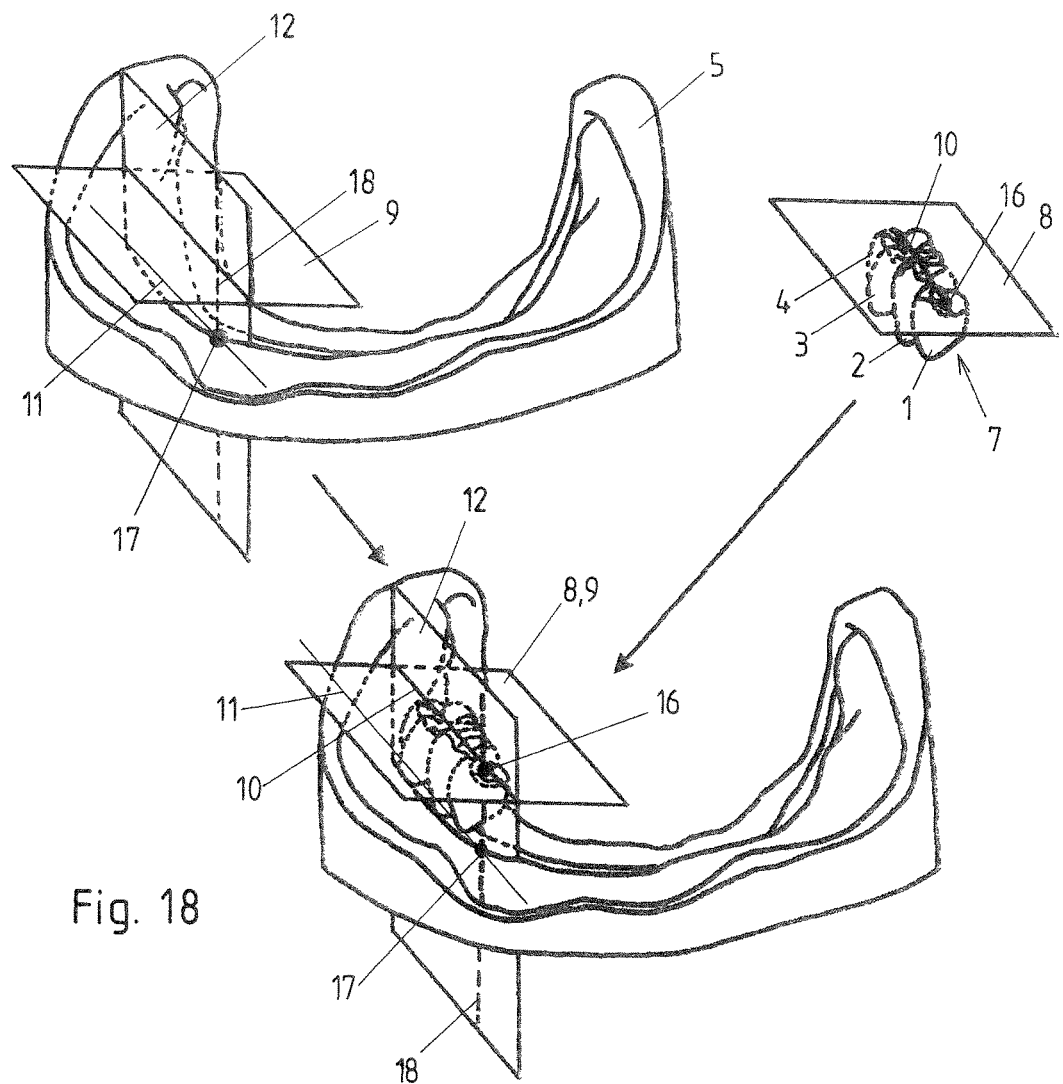
FIG. 18 shows a diagrammatic representation of the assignment, according to the invention, of the tooth block to the jaw model.

FIG. 18 shows by way of example the assignment, according to the invention, of the tooth block 7 to the jaw model 5, here of the lower jaw, using the geometric parameters determined as described above. In the jaw model 5, these are firstly the jaw model occlusion plane 9, the common base static line 11 and the jaw model 4th position 17. In the tooth block 7 in FIG. 18, only the four artificial posterior teeth 1 to 4 of the lower jaw are shown. To make the drawing easier to follow, the associated artificial posterior teeth 19 to 22 of the upper jaw of this tooth block 7 have been omitted here. However, the figure shows the tooth block occlusion plane 8, the common main fissure line 10 and the tooth 4 position 16 which, in this illustrative embodiment, form the geometric parameters of the tooth block 7. In this illustrative embodiment, the assignment according to the invention takes place by means of the geometric parameters of the jaw model 5 being made congruent with the geometric parameters of the tooth block 7. For this purpose, the tooth block occlusion plane 8 and the jaw model occlusion plane 9 are made congruent with each other. In other words, the tooth block occlusion plane 8 is placed in the jaw model occlusion plane 9. The common main fissure line 10 of the tooth block 7 and the base static line 11 are arranged in the common base static plane 12, said base static plane 12 being orthogonal with respect to the jaw model occlusion plane 9. The tooth 4 position 16 and the jaw model 4th position 17 are arranged on a common 4th straight line 18, wherein the 4th straight line 18 is arranged perpendicularly with respect to the jaw model occlusion plane 9. In this way, all the artificial posterior teeth of the tooth block 7 are assigned unambiguously to the lower jaw model 5. If, as is preferred, the tooth block 7 also comprises the antagonists of the upper jaw, then the artificial posterior teeth 19, 20, 21, 22 of the upper jaw are also positioned in this way and are positioned correctly with respect to the articulated upper jaw model 6 (not shown in FIG. 18).

The assignment is preferably carried out digitally and can take place substantially automatically. The user can then also be given the possibility of adjusting or changing the position of the tooth block 7 within the stated tolerance ranges 15 which, for the sake of clarity, are not shown in FIG. 18. A possible rule can then be provided, namely that all occlusal contact points 67 have to lie within the tolerance range 15.

Figure 19:
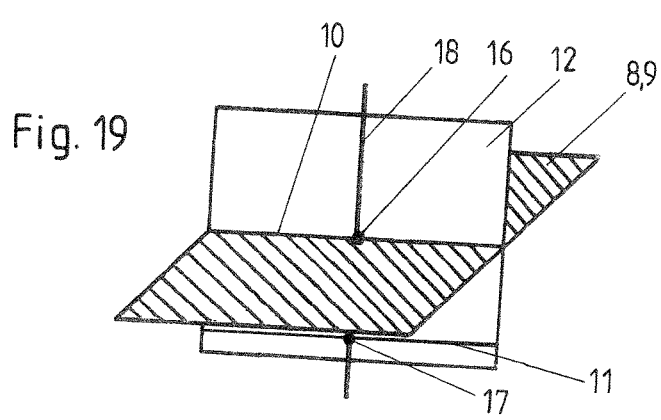
FIG. 19 shows a diagrammatic representation of the geometric parameters.
Figure 20:
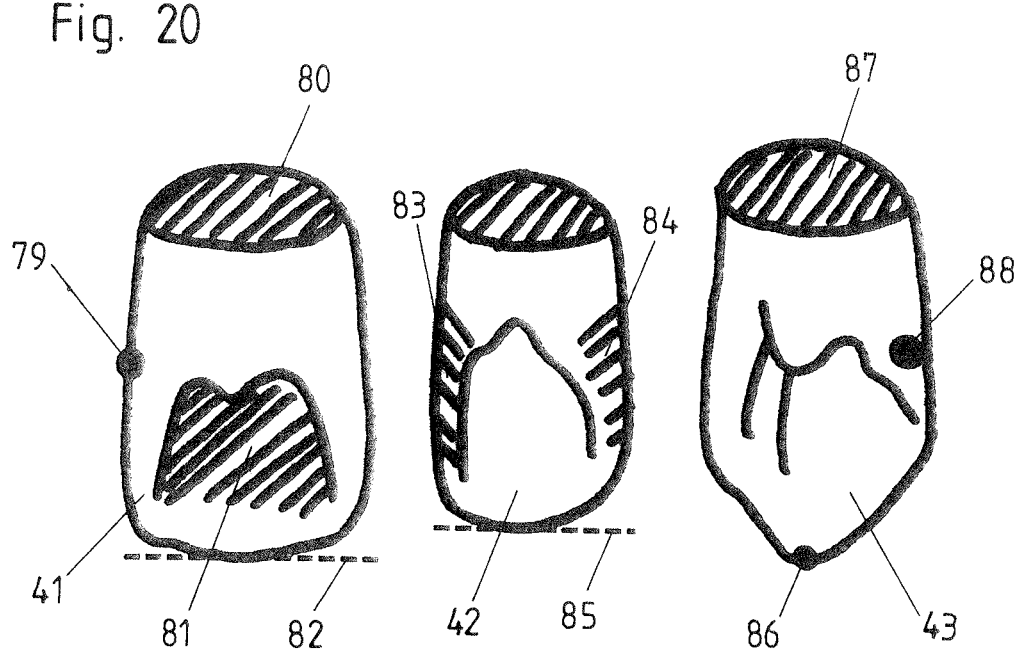
FIGS. 20 and 21 show artificial anterior teeth of the upper jaw.
Figure 21:
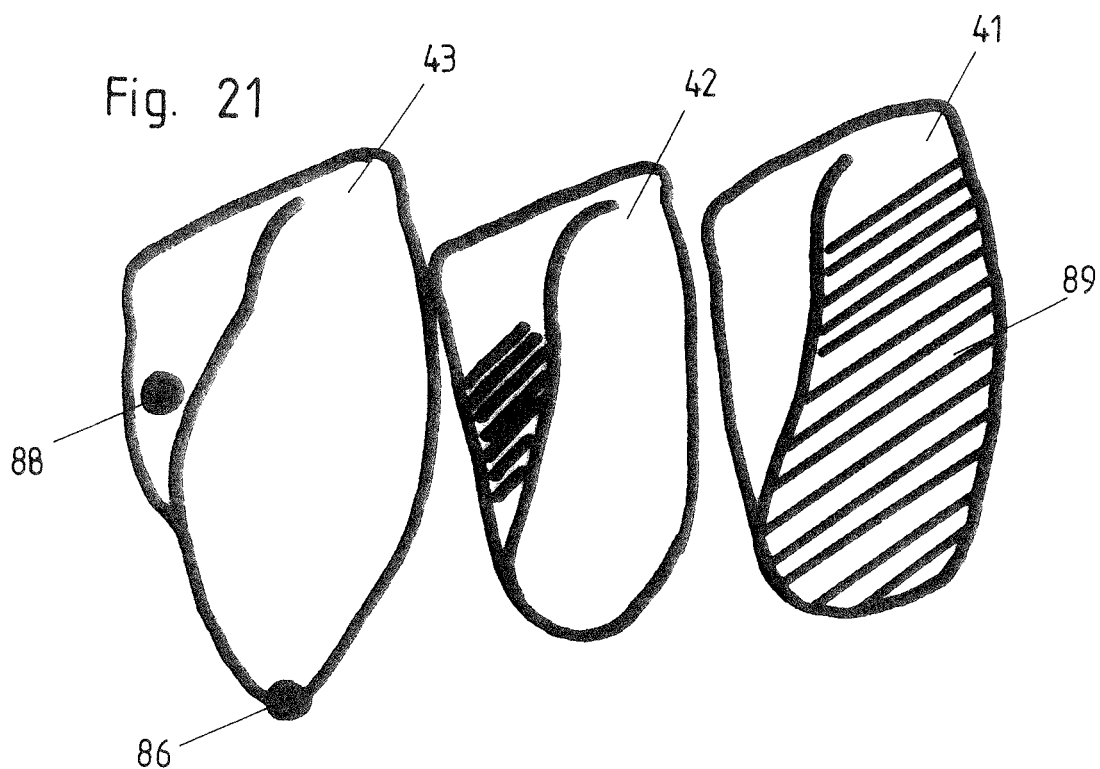
Figure 22:
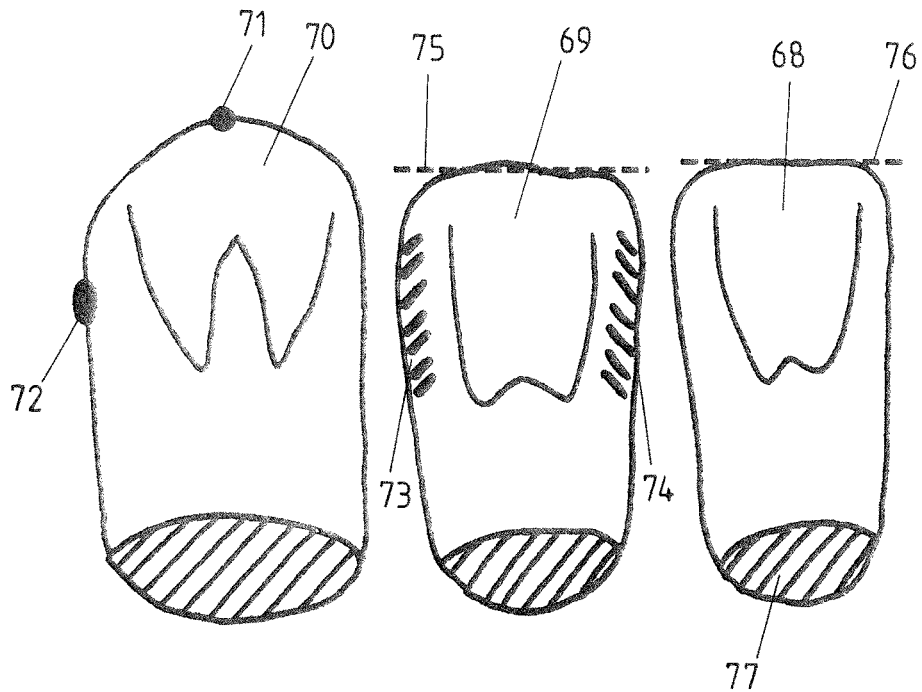
FIGS. 22 and 23 show artificial anterior teeth of the lower jaw.
Figure 23:
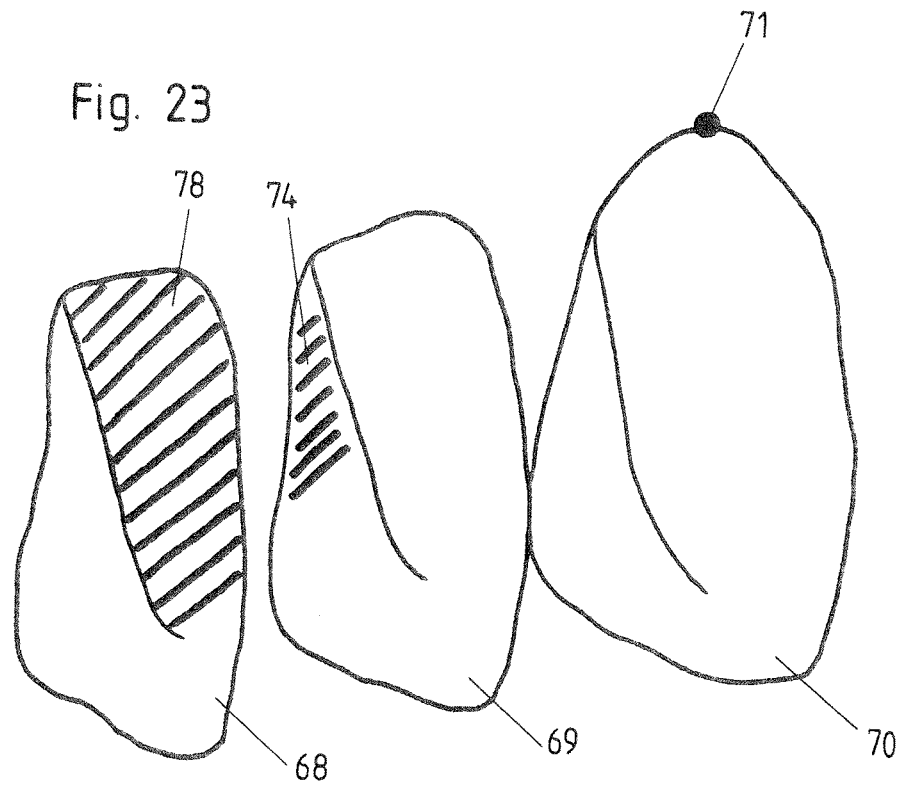

The geometric parameters used for the assignment performed according to the invention are shown once again by way of example in FIG. 19. The positioning, according to the invention, of the posterior teeth of the tooth block 7 takes place in this manner.

Following the positioning of the posterior teeth as per the invention, the positioning of the artificial anterior teeth 68, 69 and 70 of the lower jaw and of the artificial anterior teeth 41, 42 and 43 of the upper jaw is now also explained in one of many possible variants. The anterior tooth 68 is the first tooth of the lower jaw, the anterior tooth 69 is the second tooth of the lower jaw, and the anterior tooth 70 is the third tooth, i.e. the canine, of the lower jaw. In the upper jaw, reference number 41 designates the first front tooth, reference number 42 designates the second front tooth, and reference number 43 designates the third front tooth, i.e. the canine. With reference to FIGS. 20 to 23, one of various possibilities for the positioning of the artificial anterior teeth 41, 42, 43, 68, 69 and 70 on the upper jaw model 6 and lower jaw model 5, respectively, is as follows:

Thus, the first teeth 41 of the upper jaw can lie with their basal surfaces 80 on the frontal maxillary ridge center line 56 of the upper jaw model 6. The labial surfaces 89 of the first teeth 41 of the upper jaw must not exceed the maxillary labial surface limit line 57. The incisal edge 82 of the first anterior teeth 41 of the upper jaw lies 1 mm below the jaw model occlusion plane 9.

The basal surfaces 87 of the third teeth 43 of the upper jaw lie at the upper jaw 3rd position 50 of the upper jaw model 6. The distal contact point 88 of the third tooth 43 of the upper jaw must in each case touch the fourth tooth 19 of the upper jaw. The canine tip 86 of the third tooth 43 of the upper jaw lies 1 mm below the jaw model occlusion plane 9. The second teeth 42 of the upper jaw are arranged between the first teeth 41 and the third teeth 43 of the upper jaw in such a way that a harmonic arch is formed. The mesial surfaces 83 of the second teeth 42 of the upper jaw have to touch the distal surfaces of the first teeth 41 of the upper jaw, while the distal surfaces 84 of the second teeth 42 of the upper jaw have to touch the respective mesial surfaces of the third teeth 43 of the upper jaw. The incisal edges 85 of the second teeth 42 of the upper jaw lie on the jaw model occlusion plane 9.

The first teeth 68 of the lower jaw have to lie with their basal surfaces 77 on the mandibular ridge center line 40 of the lower jaw model 5. The labial surfaces 78 of the first teeth 68 must not exceed the mandibular labial surface limit line 31. The incisal edge 76 of the first tooth 68 of the lower jaw lies on the jaw model occlusion plane 9 and ideally 1 mm to 2 mm behind the lingual surface 81 of the first tooth 41 of the upper jaw. The third teeth 70 of the lower jaw lie on the alveolar ridge profile 27 of the lower jaw model 5. The distal contact point 72 of the third tooth 70 of the lower jaw has to touch the fourth tooth 1 of the lower jaw. The canine tip 71 of the third tooth 70 of the lower jaw lies 1 mm above the jaw model occlusion plane 9. The second teeth 69 of the lower jaw are arranged between the first teeth 68 of the lower jaw and the third teeth 70 of the lower jaw in such a way that a harmonic arch is formed. The mesial surface 74 of the second tooth 69 of the lower jaw has to touch the first tooth 68 of the lower jaw. The incisal edge 75 of the second tooth 69 of the lower jaw lies on the jaw model occlusion plane 9.

This is just one example of how the anterior teeth can be positioned. Particularly in the case of the anterior teeth, the described positioning can also be manipulated in order to reconstruct and reproduce individual characteristics of the original natural dentition of the patient. The positioning of the anterior teeth can be performed digitally or with computer aid. If appropriate, a corresponding interaction with the user can be provided. The anterior teeth can either be positioned individually or jointly, e.g. in a chain.

KEY TO THE REFERENCE NUMBERS 1 artificial posterior tooth
2 artificial posterior tooth
3 artificial posterior tooth
4 artificial posterior tooth
5 jaw model of the lower jaw
6 jaw model of the upper jaw
7 tooth block
8 tooth block occlusion plane
9 jaw model occlusion plane
10 main fissure line
11 base static line
11a base static line of the jaw model of the lower jaw
11b base static line of the jaw model of the upper jaw
12 base static plane
13 correction plane of the inner correction line
14 correction plane of the outer correction line
15 tolerance range
16 tooth 4 position
17 jaw model 4th position
18 4th straight line
19 artificial posterior tooth
20 artificial posterior tooth
21 artificial posterior tooth
22 artificial posterior tooth
23 distance
24 distance
25 outer mucolabial fold
26 inner mucolabial fold
27 alveolar ridge profile
28 buccal frenum
29 distance 30 distance
31 mandibular labial surface limit line
32 lower jaw 6th position
33 mandibular endpoint
34 trigone
35 center point of trigone
36 mandibular lingual frenum
37a mandibular outer correction line
37b maxillary outer correction line
38a mandibular inner correction line
38b maxillary inner correction line
39 mandibular center line
40 frontal mandibular ridge center line
41 artificial anterior tooth
42 artificial anterior tooth
43 artificial anterior tooth
44 distance
45 distance
46 incisive papilla
47 center point
48 first greater palatine fold
49 pterygomandibular fold
50 upper jaw 3rd position
51 upper jaw 4th position
52 upper jaw 6th position
53 tuber
54 center point of tuber
55 maxillary center line
56 frontal maxillary ridge center line
57 maxillary labial surface limit line
58 articulator
59 marking
60 bite plate
61 marking
62 straight line
63 angle
64 parallel
65 tooth 6 position
66 tooth endpoint
67 occlusal contact point
68 artificial anterior tooth
69 artificial anterior tooth
70 artificial anterior tooth
71 canine tip
72 distal contact point
73 distal surface
74 mesial surface
75 incisal edge
76 incisal edge
77 basal surface
78 labial surface
79 mesial contact point
80 basal surface
81 lingual surface
82 incisal edge
83 mesial surface
84 distal surface
85 incisal edge
86 canine tip
87 basal surface
88 distal contact point
89 labial surface

The invention claimed is:

1. A method, carried out digitally in part, for positioning artificial posterior teeth on an entirely edentulous or at least partially edentulous jaw model of a lower jaw, comprising: combining several artificial posterior teeth at least adapted for the lower jaw to form at least one tooth block, arranging the artificial posterior teeth in said tooth block in a fixed geometric relationship to one another, establishing geometric parameters of the tooth block on the tooth block, establishing geometric parameters of the jaw model on the jaw model, and, in order to position the tooth block on the jaw model, assigning the geometric parameters of the tooth block to the geometric parameters of the jaw model, wherein one of the geometric parameters of the tooth block is a tooth block occlusion plane common to the artificial posterior teeth of the tooth block, and one of the geometric parameters of the jaw model is a jaw model occlusion plane assigned to the jaw model, and, to position said tooth block on the jaw model, the method further comprises placing the tooth block occlusion plane in the jaw model occlusion plane, one of the geometric parameters of the tooth block is a main fissure line common to the artificial posterior teeth of the tooth block, and one of the geometric parameter of the jaw model is a base static line assigned to the jaw model, and, to position the tooth block on the jaw model, the method further comprises arranging the main fissure line and the base static line in a common base static plane, the base static plane is arranged orthogonally on the jaw model occlusion plane, and the assignment of the geometric parameters of the tooth block to the geometric parameters of the jaw model is carried out digitally, the method further comprising producing a prosthesis based on a digital model of the jaw model generated digitally along with the positioned posterior teeth.

2. The method as claimed in claim 1, further comprising, when the tooth block is positioned on the jaw model, making the geometric parameters of the tooth block congruent with the geometric parameters of the jaw model.

3. The method as claimed in claim 1, further comprising assigning the base static plane a tolerance range in which deviations of the main fissure line from the base static plane are permitted.

4. The method of claim 3, wherein the tolerance range is limited by correction planes arranged orthogonally on the jaw model occlusion plane.

5. The method as claimed in claim 1, wherein one of the geometric parameters of the tooth block is a tooth position 4 assigned to an artificial 4th tooth of the tooth block, and one of the geometric parameters of the jaw model is a jaw model 4th position assigned to the jaw model, and, when the tooth block is positioned on the jaw model, the method further comprises arranging the tooth position 4 and the jaw model 4th position on a common straight line.

6. The method as claimed in claim 5, wherein the 4th straight line is arranged perpendicularly on the jaw model occlusion plane.

7. The method as claimed in claim 1, wherein the tooth block comprises at least three artificial posterior teeth.

8. The method as claimed in claim 1, wherein the tooth block comprises artificial posterior teeth for the upper jaw assigned to the artificial teeth for the lower jaw.

9. The method of claim 1, wherein the prosthesis is produced also with positioned anterior teeth.

* * * * *